(12) United States Patent
Matsuba

(10) Patent No.: US 7,528,394 B2
(45) Date of Patent: May 5, 2009

(54) FOCUSED ION BEAM SYSTEM

(75) Inventor: Masahiro Matsuba, Tokyo (JP)

(73) Assignee: Jeol Ltd., Tokyo (JP)

( * ) Notice: Subject to any disclaimer, the term of this patent is extended or adjusted under 35 U.S.C. 154(b) by 103 days.

(21) Appl. No.: 11/417,504

(22) Filed: May 4, 2006

(65) Prior Publication Data

US 2006/0289801 A1 Dec. 28, 2006

(30) Foreign Application Priority Data

May 9, 2005 (JP) ............... 2005-136463

(51) Int. Cl.
*G21K 5/04* (2006.01)
(52) U.S. Cl. ............... 250/492.3; 250/396 R; 250/396 ML; 250/309
(58) Field of Classification Search ........... 250/309, 250/396 R, 396 ML, 492.1, 492.2, 492.21, 250/492.22, 492.3
See application file for complete search history.

(56) References Cited

U.S. PATENT DOCUMENTS

| | | | | |
|---|---|---|---|---|
| 5,124,556 A | * | 6/1992 | Takashima | 250/396 R |
| 6,459,082 B1 | * | 10/2002 | Sakaguchi | 250/309 |
| 7,242,013 B2 | * | 7/2007 | Fukuda et al. | 250/492.2 |
| 2005/0066899 A1 | * | 3/2005 | Fukuda et al. | 118/723 FI |

FOREIGN PATENT DOCUMENTS

| | | | |
|---|---|---|---|
| JP | 7-37538 | | 7/1995 |
| JP | 07201299 A | * | 8/1995 |
| JP | 2001351561 A | * | 12/2001 |

OTHER PUBLICATIONS

Fu, et al ("Investigation of integrated diffractive/refractive microlens microfabricated by focused ion beam" Rev. Sci. Instrum. 71(6) Jun. 2000 pp. 2263-2266).*

* cited by examiner

*Primary Examiner*—David A Vanore
*Assistant Examiner*—Michael Maskell
(74) *Attorney, Agent, or Firm*—The Webb Law Firm

(57) ABSTRACT

A focused ion beam (FIB) system that can automatically set processing and scanning conditions under which a specimen is processed includes an arithmetic unit for selecting optical conditions for condenser lenses, multiple variable apertures, beam-deflecting electrodes, and an objective lens based on data entered into the input device. The arithmetic unit automatically calculates the processing and scanning conditions under which the specimen is processed by the focused ion beam, according to the selected-optical conditions. The system further includes a setting condition data output portion for outputting data based on the optical conditions and processing and scanning conditions selected and calculated by the arithmetic unit. The system further includes a FIB driver portion for driving the condenser lenses, beam-blanking electrodes, apertures, deflecting electrodes, and objective lens based on the optical conditions and processing and scanning conditions outputted from the data output portion.

8 Claims, 7 Drawing Sheets

| FILE NUMBER | BEAM DIAMETER | LENS SYSTEM | APERTURE | DEFLECTION SYSTEM |
|---|---|---|---|---|
| BEAM 1 | $\phi 1$ | a1, b1 | N1 | x1, y1 |
| BEAM 2 | $\phi 2$ | a2, b2 | N2 | x2, y2 |
| BEAM 3 | $\phi 3$ | a3, b3 | N3 | x3, y3 |
| BEAM 4 | $\phi 4$ | a4, b4 | N4 | x4, y4 |
| . | . | . | . | . |
| . | . | . | . | . |
| . | . | . | . | . |
| . | . | . | . | . |
| BEAM 10 | $\phi 10$ | a10, b10 | N10 | x10, y10 |

FOCUSED ION BEAM SYSTEM

BACKGROUND OF THE INVENTION

1. Field of the Invention

The present invention relates to a focused ion beam (FIB) system for processing a specimen by directing a focused ion beam at the specimen and, more particularly, to a FIB system which calculates the processing conditions while the operator is monitoring the specimen after optical conditions are selected.

2. Description of Related Art

A FIB system is a tool for processing a specimen by sharply focusing an ion beam produced from an ion source and directing the beam at the specimen so as to etch it. Among applications of such FIB systems, etching techniques relying on FIB have become widely spread.

FIB systems using these techniques are widely used in defect analysis of semiconductor devices and specimen preparation in transmission electron microscopy as well as in micromachining. Especially, in three-dimensional analysis of semiconductor devices that has attracted the greatest attention, FIB systems are becoming indispensable tools.

FIG. 1 shows the structure of a FIB system. The inside of the body 1 of the system is evacuated. The body 1 has a specimen chamber 1a in which a specimen stage 3 is placed. A specimen 2, such as a semiconductor device, is placed on the stage 3. Also contained in the body 1 are an ion source 5 for producing an ion beam 4, an extraction electrode 6 for extracting ions from the ion source 5, accelerating electrodes 7, condenser lenses 8 for focusing the ion beam, beam-blanking electrodes 9, multiple variable apertures 10, beam-deflecting electrodes 11 for scanning the ion beam in two dimensions, and an objective lens 12. A detector 13 for detecting secondary charged particles produced from the specimen 2 is also installed in the specimen chamber 1a. Electrostatic lenses are used for the condenser lenses 8 and objective lens 12.

Some components (e.g., condenser lenses 8, multiple variable apertures 10, beam-deflecting electrodes 11, and objective lens 12) of the body 1 of the FIB system are driven by a FIB driver portion 14 that is under control of a computer 15. The computer 15 has an arithmetic unit 16, an input device 17, and a monitor 18 (e.g., a cathode-ray tube (CRT) or liquid crystal display (LCD)). The arithmetic unit 16 has RAM and HDD which are incorporated therein or attached thereto.

For example, where the amount of current of the ion beam hitting the specimen 2 is varied, the FIB driver portion 14 controls the condenser lenses 8 and objective lens 12 to control the intensities of the lenses. This varies the degree of focusing of the beam. An appropriate aperture is selected from the multiple variable apertures 10 mounted in the optical path of the ion beam 4. In this way, the amount of the passing ion beam is controlled. Where the ion beam 4 is scanned over the specimen 2 in two dimensions or raster-scanned, a scan signal is supplied to the beam-deflecting electrodes 11 from the FIB driver portion 14.

The specimen 2 is placed on the specimen stage 3. The stage 3 is designed to be capable of being moved in two dimensions within a horizontal plane, rotated, and tilted by a stage control portion 19, which is under control of computer 15.

Ions are extracted from the ion source 5 by the extraction electrode 6. The ions are accelerated by the accelerating electrodes 7. The ion beam 4 of the accelerated ions is sharply focused onto the specimen 2 by the condenser lenses 8 and objective lens 12. The beam position on the specimen 2 is scanned by supplying the scan signal to the beam-deflecting electrodes 11. As a result, a desired portion of the specimen is cut or processed by the ion beam.

The intensity of the ion beam 4 is controlled by the computer 15 via the FIB driver portion 14 such that the specimen 2 is not processed. The beam is scanned over the specimen 2 in two dimensions. Secondary electrons emanating from the specimen 2 are detected by the secondary electron detector 13. Image processing is performed by the arithmetic unit 16 of the computer 15 and then a secondary electron image is displayed on the monitor 18.

Today, dual-beam systems each consisting of a conventional in-line scanning electron microscope (SEM) to which FIB capabilities are added have also become widespread. The dual-beam systems are described, for example, in Japanese Patent Laid-Open No. H7-37538.

A dual-beam system (FIB/SEM instrument) is a combined instrument capable of playing the role of the conventional FIB instrument that etches a specimen as a semiconductor defect analysis tool and then moves the specimen onto a SEM to observe the specimen.

This combined instrument has the advantage that it can perform SEM imaging similarly to an ordinary, single-function FIB machine. That is, an ion beam is directed at the top surface of a specimen. A desired portion is etched. After completion of the etching, the etched cross section can be immediately observed as an SEM image without moving the specimen. As a result, the combined instrument exhibits excellent capabilities in defect analysis and shortens the process sequence time. Concomitantly, the yield management can be done at an improved rate. Furthermore, the combined instrument has a small footprint because of the combined capabilities. The cost can also be reduced.

The above-described FIB/SEM instrument roughly consists of a FIB control portion, a SEM control portion, and a stage control portion for controlling a specimen stage. These portions are controlled by a computer. The FIB instrument etches a specimen by directing an ion beam at the specimen such that the beam impinges on the specimen normally from vertically above it under the control of the computer. In the SEM, an electron beam impinges on the cross section of the formed hole at an angle of 30° with respect to the specimen surface to permit observation of the cross-sectional morphology.

Where milling is done by a FIB system, it has been heretofore necessary to manually set parameters or select an appropriate setting file and utilize it. The parameters include (1) the size of the processed region, (2) the intensity of the used ion beam, (3) the depth of the cut hole and the kind of the specimen or the dose of the illuminating ion beam, and (4) processing and scanning conditions (dwell time (DT) per hit point and the dwell point spacing (DPS)).

However, manual setting of the parameters (1)-(4) above or selection of an appropriate setting file depends on the knowledge and experience of each individual operator of the FIB system. Therefore, much labor and time are required to set the parameters. Furthermore, if different operators set different parameters in processing the same material, different processing results will arise. In addition, if any set parameter is disabled because of the hardware limitation, the settings are invalidated.

SUMMARY OF THE INVENTION

It is an object of the present invention to provide a focused ion beam (FIB) system capable of automatically setting processing and scanning conditions (processing/scanning conditions) when a specimen is processed.

A focused ion beam system associated with an embodiment of the present invention solves the foregoing problems and processes a specimen by directing a focused ion beam at the specimen. This system comprises an ion beam source for producing the ion beam, condenser lenses for focusing the produced ion beam, multiple variable apertures for selectively limiting the electrical current of the ion beam focused by the condenser lenses, a deflection portion for deflecting the focused ion beam whose current has been selectively limited by the apertures, an objective lens for focusing the deflected ion beam onto the specimen at a desired location, a specimen stage for moving the specimen, an input portion for accepting data entered by a human operator, a control portion, a setting condition data output portion, and a driver portion. The control portion selects optical conditions for the condenser lenses, multiple variable apertures, deflection portion, and objective lens based on the data entered into the input portion. The control portion also automatically calculates processing and scanning conditions of the focused beam on the specimen according to the selected optical conditions. The setting condition data output portion outputs data based on the optical conditions and the processing and scanning conditions selected and calculated by the control portion. The driver portion drives the condenser lenses, variable apertures, deflection portion, and objective lens based on the optical conditions and processing/scanning conditions outputted from the setting condition data output portion.

In this FIB system, the control portion preferably calculates the processing and scanning conditions automatically according to the size of the observed region on the specimen entered into the input portion. Furthermore, the control portion preferably sets the dwell time of the ion beam on one point on the specimen and the dwell point spacing automatically as the processing and scanning conditions.

Furthermore, in this FIB system, the control portion preferably calculates the diameter of the ion beam used for processing according to the size of the processed region of the specimen entered into the input portion, and selects an optical condition file matched to the diameter of the beam. In addition, the control portion preferably selects the optical condition file automatically based on the calculated diameter of the beam, the file defining a mode of operation in which the condenser lenses, objective lens, multiple variable apertures, and deflection portion are driven by the driver portion.

The FIB system, according to the present invention, automatically calculates and sets the diameter of the ion beam used for processing according to the "size of the processed region" entered by the operator in this way. Furthermore, the system automatically calculates and sets the diameter of the ion beam used for processing according to the "degree of finish" of the processed specimen. In addition, the system automatically calculates and sets beam processing and scanning conditions (i.e., (1) dwell time (DT) per hit point and (2) dwell point spacing (DPS)) according to the diameter of the used ion beam. Additionally, the system automatically calculates and sets the beam processing and scanning conditions (i.e., (1) dwell time (DT) per hit point and (2) dwell point spacing (DPS)) according to the depth of the processed region and dose. Of course, these functions may be appropriately combined.

The FIB system associated with the present invention can automatically set processing and scanning conditions under which a specimen is processed. That is, beam diameter, dwell time per hit point, and dwell point spacing used for the processing are calculated and automatically set according to the size of the processed region and the degree of finish that the operator wants. Furthermore, the dwell point spacing used when the ion beam is scanned is automatically calculated and set optimally according to the used ion beam. Consequently, it is possible to prevent such a situation that a dwell point spacing that is too wide for the beam diameter is set; otherwise, the processed surface would be made discontinuous. Additionally, the dwell time per hit point and dwell point spacing which reduce the number of frames used for processing down to a bare minimum are automatically calculated and set optimally. Consequently, damage to the specimen caused by blanking tail can be minimized. Further, deterioration of the finished shape can be prevented because the dwell time per hit point and dwell point spacing are automatically calculated and set optimally.

Other objects and features of the invention will appear in the course of the description thereof, which follows.

DESCRIPTION OF THE PREFERRED EMBODIMENTS

The best mode for carrying out the present invention is hereinafter described. This mode is a focused ion beam (FIB) system that can be widely applied to defect analysis of semiconductor devices and specimen preparation in transmission electron microscopy (TEM), as well as to micromachining.

Figure 1:
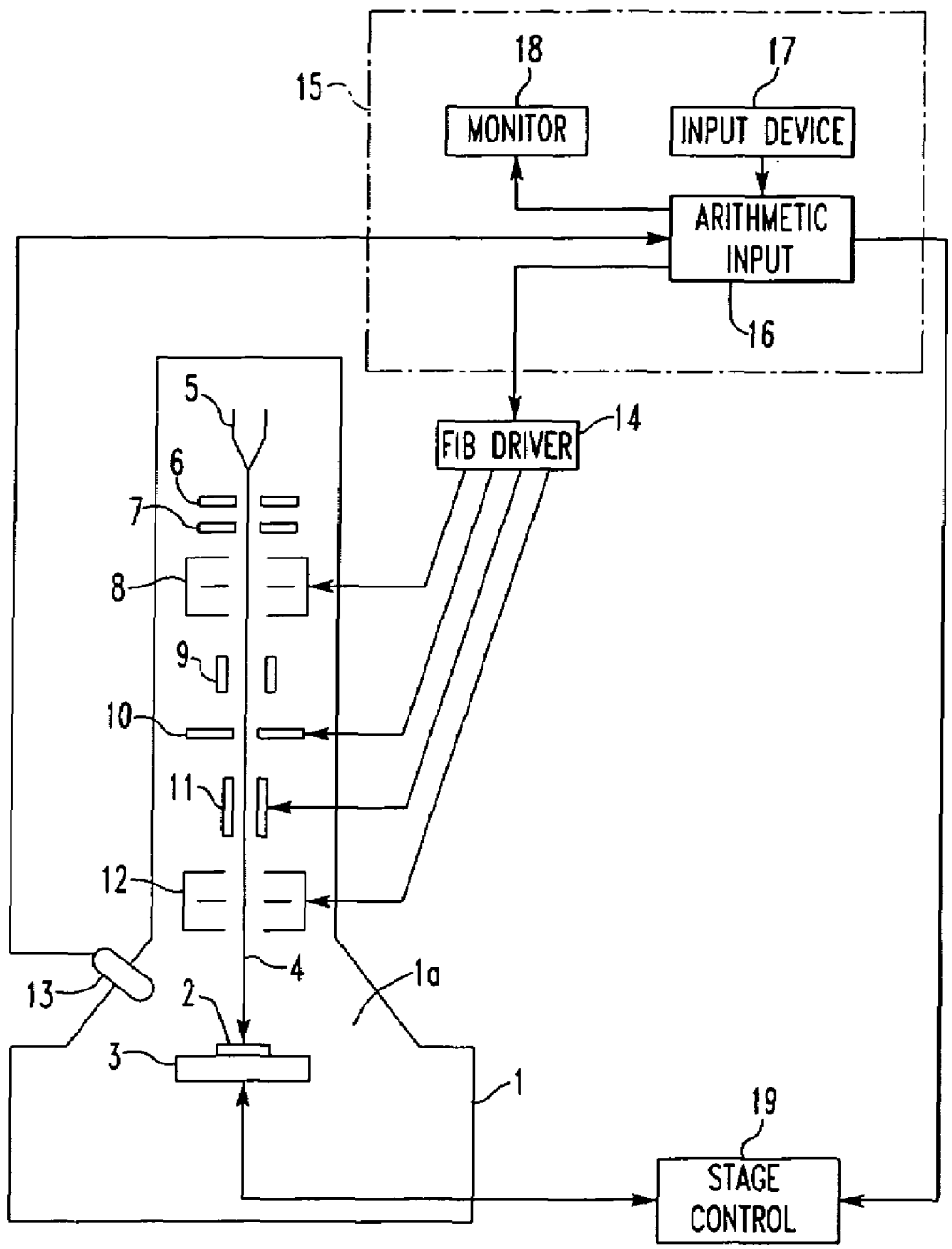
FIG. 1 is a block diagram of a prior art FIB system.
Figure 2:
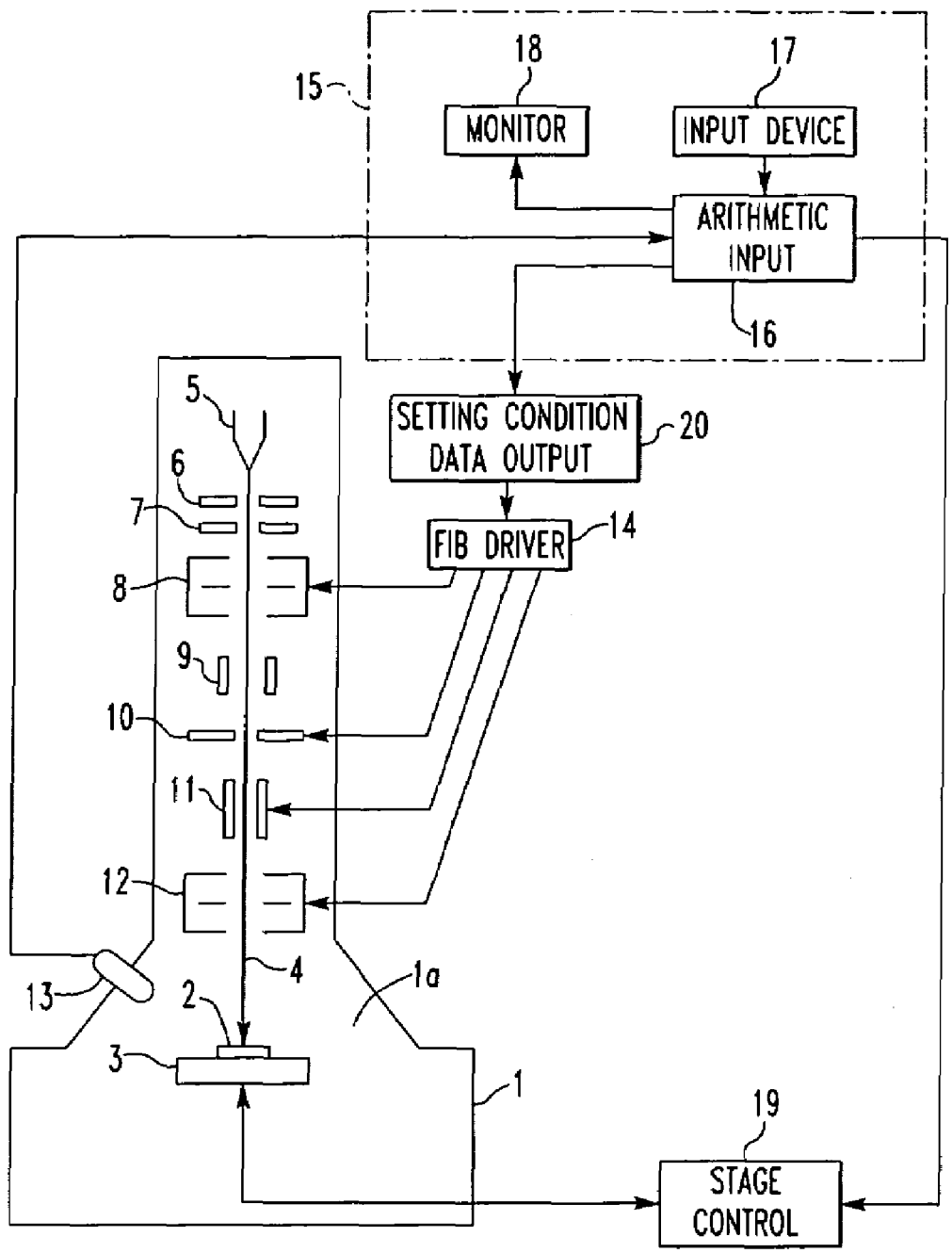
FIG. 2 is a block diagram of a FIB system according to an embodiment of the present invention.

FIG. 2 shows the structure of the FIB system. This system is similar to the prior art FIB system already described in connection with FIG. 1 except that a computer 15 selects optical conditions (described later) according to data entered by the operator indicating the size of the processed region and the degree of finish of the processed material and that the computer automatically sets processing and scanning conditions (described later) according to the size of the observed region indicated by data entered by the operator. The resulting data are supplied to a setting condition data output portion 20.

The body 1 of the FIB system has an ion beam source 5, an extraction electrode 6, accelerating electrodes 7, condenser lenses 8, beam-blanking electrodes 9, multiple variable apertures 10, beam-deflecting electrodes 11, and objective lens 12. A specimen 2 is placed on a specimen stage 3 within a specimen chamber 1a.

The FIB system further includes the computer 15 made up of an arithmetic unit 16, an input device 17 connected with the arithmetic unit 16, and a monitor 18 connected with the arithmetic unit. The FIB system further has the FIB driver portion 14 for driving given internal parts of the body 1 in accordance with the set condition data from the setting condition data output portion 20 that is mounted between the arithmetic unit 16 and the FIB driver portion 14. The FIB system is further equipped with a stage control portion 19 for controlling the specimen stage 3.

Inside the body 1 of the FIB system, the ion beam source 5 produces an ion beam 4. The extraction electrode 6 extracts ions from the ion source 5. Acceleration electrodes 7 accelerate the ions, which have been extracted from the ion source 5 by the extraction electrode 6. The condenser lenses 8 focus the ion beam produced by the ion beam source 5.

The beam-blanking electrodes 9 turn on and off the impingement of the ion beam 4 focused on the specimen 2 by the condenser lenses 8. The multiple variable apertures 10 selectively limit the current of the ion beam that is made to impinge on the specimen by the blanking electrodes 9. The beam-deflecting electrodes 11 deflect the focused ion beam 4 whose current has been selectively limited by the multiple variable apertures 10. The objective lens 12 focuses the ion beam 4, which has been deflected by the deflecting electrodes 11, at a given position on the specimen 2. The specimen stage 3 moves the specimen 2 in two dimensions within a horizontal plane, rotates the specimen, or tilts it.

The input device 17 accepts data entered by the operator. The arithmetic unit 16 selects optical conditions for the condenser lenses 8, variable apertures 10, beam deflecting electrodes 11, and objective lens 12 based on the data entered into the input device 17. The arithmetic unit 16 also automatically calculates the processing and scanning conditions under which the ion beam 4 is scanned to process the specimen 2, according to the selected optical conditions. The setting condition data output portion 20 outputs data based on the optical and processing/scanning conditions selected and calculated by the arithmetic unit 16. The FIB driver portion 14 drives the condenser lenses 8, blanking electrodes 9, apertures 10, deflecting electrodes 11, and objective lens 12 based on the optical and processing/scanning conditions outputted from the setting condition data output portion 20.

Figure 3:
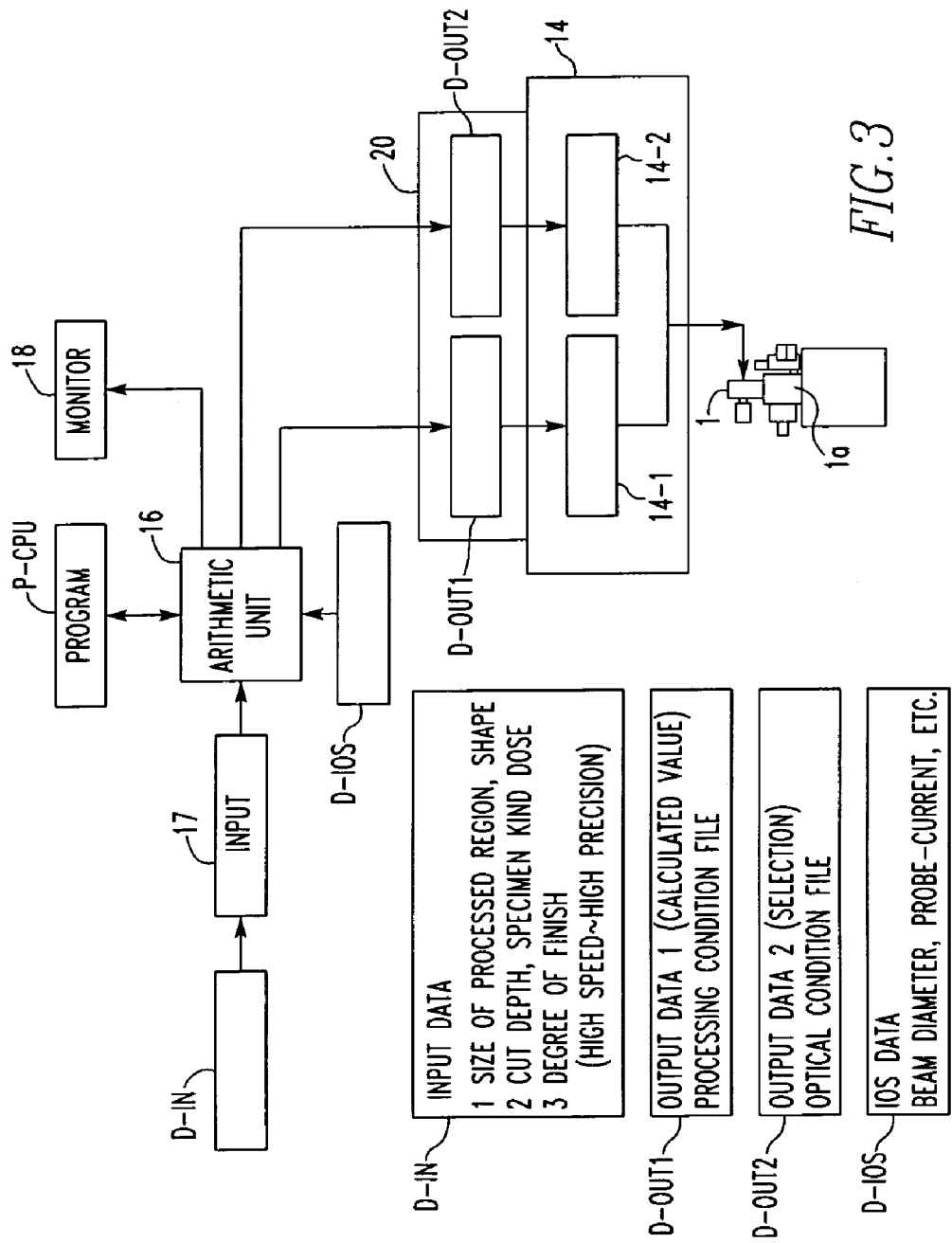
FIG. 3 is a diagram illustrating a computer and a setting condition data output portion, as well as data processing and control performed by a FIB driver portion.

FIG. 3 illustrates the manner in which data processing and control are performed by the computer 15, setting condition data output portion 20, and FIB driver portion 14. Plural optical condition files have been previously registered in a storage portion (not shown) of the arithmetic unit 16 of the computer 15.

Figures 4, 5:
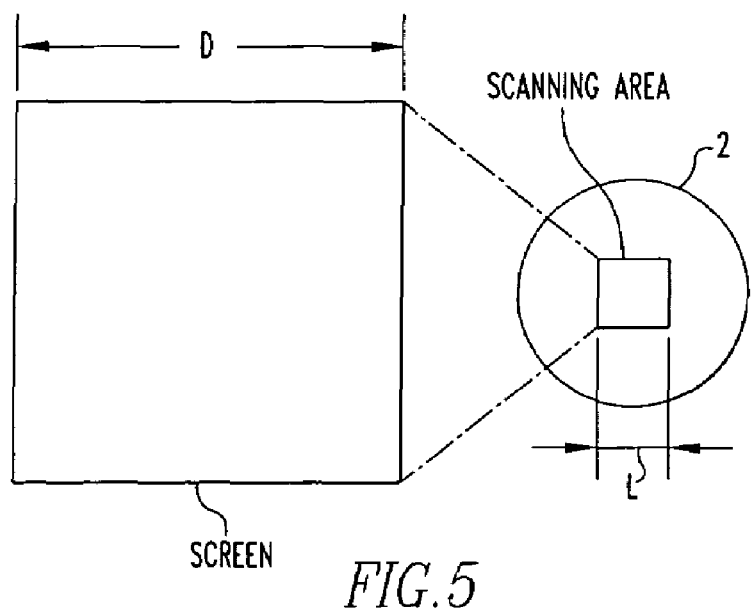
FIG. 4 is a table illustrating an optical condition table.
FIG. 5 illustrates the magnification.

FIG. 4 is a table illustrating the optical condition files in which sets of control data about the lenses, deflection system, and multiple movable apertures necessary to obtain various ion beam diameters are stored in a corresponding manner to file numbers.

Optical condition file numbers "beam 1" to "beam 10" are assigned in the order of increasing or reducing the beam diameter. With the optical file condition number "beam 1", the lenses, apertures, and deflection system are set to obtain a beam diameter of $\phi 1$. With optical condition file numbers "beam 2" to "beam 10", the lenses and so on are set to have beam diameters of $\phi 2$ to $\phi 10$.

In FIG. 3, if the operator enters the size of the processed region (1) as input data D-IN into the input device 17, the arithmetic unit 16 of the computer 15 calculates the used beam diameter from the input data. The "size of the processed region" is the size of a region on the specimen that the operator wants to have by means of processing using the ion beam. The arithmetic unit 16 executes a program for finding the beam diameter from the processed region size specified by the operator. The beam diameter is calculated by the calculational program based on the ratio to the side (width) of the rectangle of the size of the processed region entered by the operator. For example, if the width of the rectangle is 10 µm, the ratio is 1/10. The beam diameter is calculated to be 1 µm.

An "optical condition file" having a beam diameter closest to the calculated beam diameter is automatically selected as a reference file.

Then, the operator enters data about the "degree of finish" as input data D-IN from the input device 17. "Optical condition files" having beam diameters approximate to (slightly greater and smaller than) the beam diameter assumed in the reference file are selected. The "degree of finish" is a setting regarding the niceness and accuracy of ion beam processing that the operator wants. This is a qualitative set item including shear droop at edges caused during cutting operation. For example, where a file of "beam 3" shown in FIG. 4 is selected as the reference file, files placed around the file of "beam 3" are selected based on the data about the degree of finish. That is, any one of files of "beam 2" and "beam 4" is selected based on the data about the degree of finish.

In particular, the beam diameter is determined as a reference diameter from the size of the region. Beam diameters which are respectively slightly larger and smaller than the reference diameter are selected according to the degree of finish selected by the operator. Optical conditions are necessary which are used (i) to determine the current values supplied to the lenses including the condenser lenses 8 and objective lens 12 of the electrostatic type in order to make the focused ion beam have the calculated beam diameter, (ii) to determine which of the multiple variable apertures 10 is selected, (iii) or to determine the current supplied to the deflecting electrodes 11. Therefore, an optical condition file is automatically selected by the computer 15. The selection depends on the beam diameter. As the beam diameter is increased, the beam intensity is also increased. Therefore, where a focused ion beam having a larger diameter is used (i.e., an intenser beam is used), the specimen can be processed in a shorter time than where a focused ion beam having a smaller diameter is used.

In this way, sets of optical condition files are selected according to entered information about the size of the processed region and about the degree of finish. The arithmetic unit 16 calculates the used beam diameter based on input conditions about the "size" of the processed region. An optical condition file having a beam diameter closest to the result of calculation is selected as a reference. Furthermore, optical condition files having beam diameters respectively slightly greater and smaller than the reference beam diameter are selected based on the settings on the "degree of finish".

The processing and scanning conditions define the dwell time (DT) per hit point when the specimen 2 is irradiated with a focused ion beam, the dwell point spacing (DPS), and the number of frames.

The processing and scanning conditions calculated by the arithmetic unit 16 are set using information (i.e., the size of the processed region, cut depth+specimen kind, or dose) entered by the operator. In the present embodiment, the processing and scanning conditions are calculated as follows. In fundamental scanning, the dwell point spacing is based on a frame of microscope image accepted for setting of a processed region. The dwell point spacing obtained where the resolution of the microscope image is 2,560×1,920 pixels is used as default dwell point spacing for processing. For example, a dwell time per hit point of 1 µs is used as a default dwell time. The default processing and scanning conditions set as described above are modified using conditional formulas (described later). Thus, actually used processing and scanning conditions are calculated. Accordingly, in the present method, the processing and scanning conditions are fundamentally different among different processed regions.

The arithmetic unit 16 calculates the processing and scanning conditions. After selecting the above-described optical condition file, the operator enters data D-IN from the input device 17 as shown in FIG. 3. The entered data include (1) the size of the processed region, (2) cut depth and specimen kind, or (3) dose. The arithmetic unit 16 performs calculations using a calculational program P-CPU and IOS data D-IOS offered by the optical condition file. The "cut depth+specimen kind" or "dose" is an input item determining the cut depth that the operator wants. Thus, the amount of electric charge (dose×area of the processed region) implanted into the processed region is computed. The dose is the number of ion beams implanted to a given area.

The size of the processed region is a region that is scanned by the ion beam in two dimensions. This is associated with the magnification of the observed microscope image. In this embodiment, the microscope image is made up of 2,560×1,920 pixels. The size of the processed region is specified by the operator.

FIG. 5 illustrates the ratio of the width D of the displayed microscope image to the scanning width L of the focused ion beam on the specimen 2 corresponding to the width D, the image being formed by detecting secondary electrons emanating from the specimen 2 when the ion beam is scanned over the specimen 2 in two dimensions. The ratio is referred to as the scanning magnification or simply as the magnification.

The dwell time (DT) and the dwell point spacing (DPS) that are the processing-and-scanning conditions are determined as default conditions, depending on the magnification of the microscope image of the specimen viewed by the operator. That is, DT and DPS are determined according to the size of the observed region.

The calculational program P-CPU consists of plural calculational formulas. Optimum setting values for processing conditions corresponding to the input data D-IN specifying the observed region are calculated for each processed region. The dose was found at the previous step. Therefore, the amount of ions implanted into a unit area can be computed. Then, the processing and scanning conditions can be automatically calculated from the computed amount. In the case of an unknown specimen for which the processing rate is not set, the dose may be directly entered instead of the depth and specimen as described later.

This method is different from the method adopted in the prior art product (i.e., set values judged to be appropriate according to input data are selected from a finite number of preset data sets). The output data indicative of the results of calculations performed by the arithmetic unit 16 are used for control of processing and scanning and for IOS control. IOS data are held in the aforementioned plural (e.g., ten) optical condition files, and are previously stored in the arithmetic unit 16 as data for adjusting the system.

Referring to FIG. 3, processing and scanning conditions (output data 1) D-OUT1 calculated by the arithmetic unit 16 using the calculational program P-CPU are supplied to the processing and scanning control portion 14-1 of the FIB driver portion 14 by the setting condition data output portion 20. The processing and scanning control portion 14-1 drives the condenser lenses 8, beam-blanking electrodes 9, multiple variable apertures 10, beam-deflecting electrodes 11, and objective lens 12 inside the body 1 of the FIB system to obtain the dwell time (DT) per hit point, dwell point spacing (DPS), and the number of frames which are stipulated in the processing condition file (output data 1) D-OUT1.

The reference file selected from the optical condition files previously held in the arithmetic unit 16 is outputted as output data 2D-OUT2 to the setting condition data output portion 20 and supplied to the optical control portion 14-2 of the FIB driver portion 14. The optical control portion 14-2 sets the optical lens system, apertures, and deflection system to obtain a desired beam diameter based on the output data 2D-OUT2.

Figure 6:
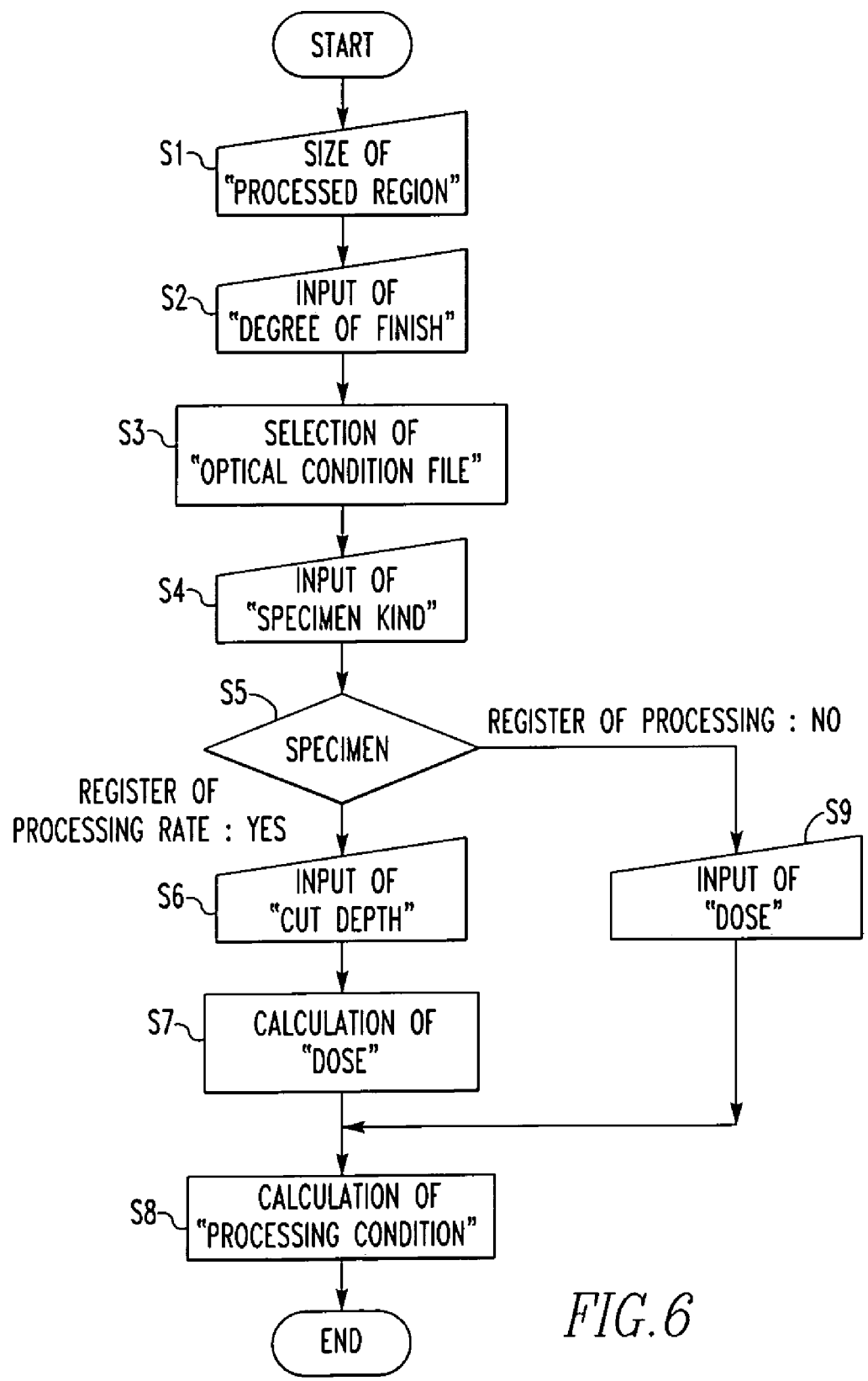
FIG. 6 is a flowchart illustrating an operation performed by the computer to select an optical condition file and a subsequent sequence of operations to calculate processing and scanning conditions.

FIG. 6 is a flowchart illustrating selection of the optical condition file performed by the computer 15 and a subsequent sequence of operations for calculating the processing and scanning conditions.

First, the operator is prompted to enter a processed region size from the input device 17 (step S1). Then, the operator is prompted to enter a degree of finish (step S2).

The arithmetic unit 16 calculates the ion beam diameter according to the entered size of the processed region and selects an optical condition file in which the calculated ion beam diameter is assumed, as a reference file from previously stored ten optical condition files. In step S2, a degree of finish indicating high speed or high accuracy has been entered and so the arithmetic unit 16 selects files adjacent to the reference file according to the degree of finish (step S3).

In step S4, the operator is prompted to enter a kind of specimen 2. Since the processing speed is different according to different kinds of specimen, entry of the kind of the specimen is required. The processing time differs according to the specified depth and specimen kind. The processing speed determining the cut depth is preset by the operator according to the specimen kind. Therefore, a decision is made as to whether the processing speed for the kind of specimen entered in step S4 has been registered (step S5). If the decision is affirmative (Yes), control goes to step S6, where a cut depth is automatically entered. Then, the dose is automatically calculated according to the depth (step S7). Then, DT and DPS are calculated automatically as the processing and scanning conditions (step S8).

If the decision at step S5 is that the processing rate for the specimen entered at step S4 is not registered, the operator is prompted to enter the dose manually (step S9).

Figure 7:
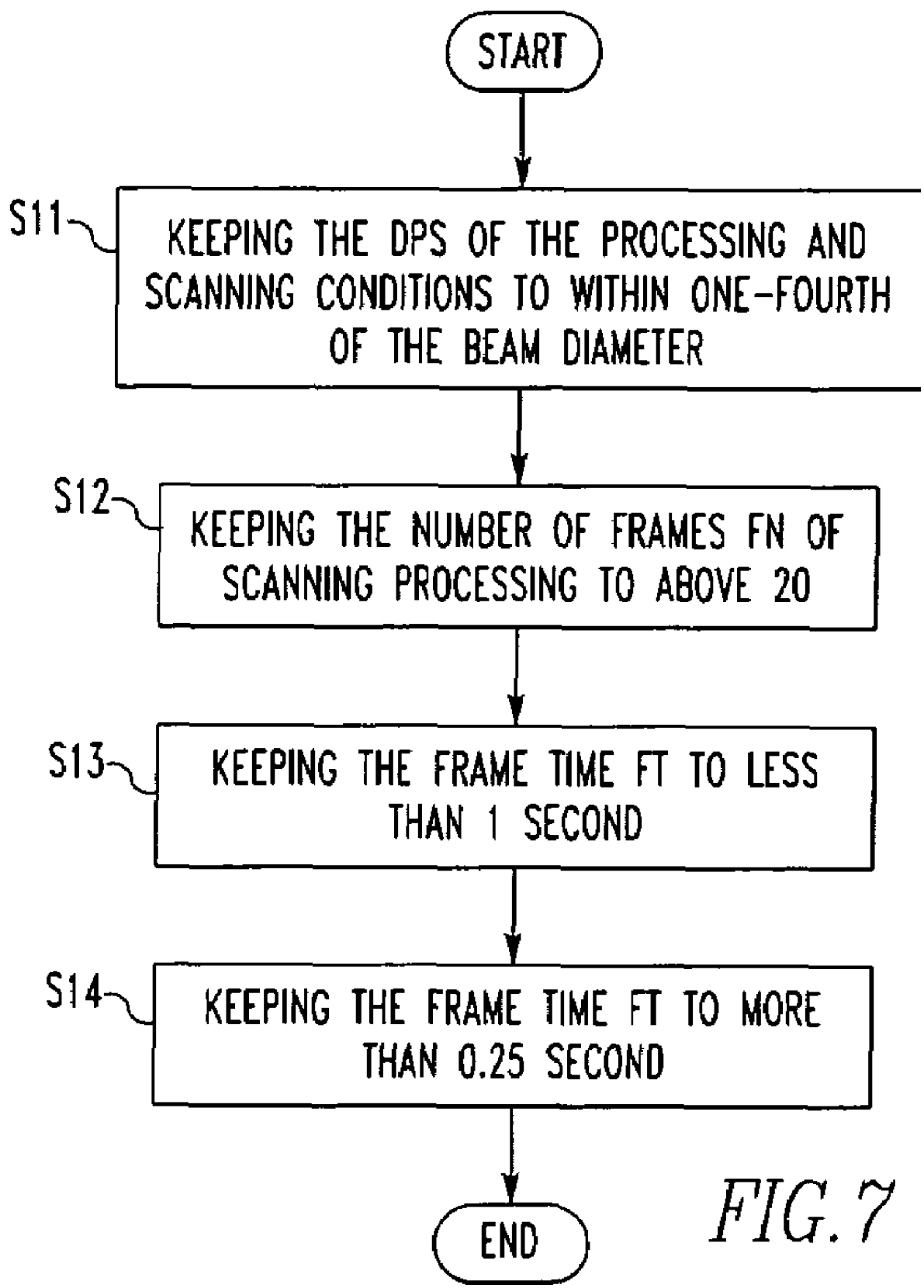
FIG. 7 is a flowchart illustrating processing for correcting processing and scanning conditions.

A sequence of operations for correction performed after the calculation of the processing and scanning conditions and its purpose are next described by referring to Table 1 and FIG. 7. In FIG. 7, the sequence of operations for correction is shown as steps S11 to S14 in the order of priority given to correction.

TABLE 1

| Purpose | Solution |
| --- | --- |
| To form clean shape by processing | a) (processing DPS) $\leq 0.25$ (beam diameter) <br> b) $20 \leq FN$ |
| To increase the speed at which real-time monitor screen is updated | c) $FT \leq 1$ s |
| To reduce blanking tail | d) $0.25$ s $\leq FT$ |

First, the DPS (dwell point spacing) of the processing and scanning conditions is kept to within one-fourth of the beam diameter (step S11). In other words, more than ¾ of the beam diameter overlaps. This prevents undulations of the shapes formed by processing, as well as formation of porous cavities.

Then, the number of frames FN of scanning processing is kept above 20 (step S12) to prevent distortion of the shape obtained by processing and prevent the cut depth from ramping. Then, the number of frames FT is kept to less than 1 second such that the image on the real-time monitor is constantly updated quickly (step S13). To make the frame time (FT) have a value of more than 0.25 second, the number of frames is suppressed to prevent the number from becoming excessively large (step S14). This suppresses the effects of the blanking tail during scanning for processing.

As described thus far, the FIB system of the structure shown in FIG. 2 automatically calculates and sets the ion beam diameter used for processing, according to the "size of the processed region" entered by the operator. Furthermore, the system automatically calculates and sets the ion beam diameter used for processing according to the "degree of finish". In addition, the beam processing and scanning conditions (i.e., (1) dwell time (DT) per hit point and (2) dwell point spacing (DPS)) are automatically calculated and set according to the used ion beam diameter. Furthermore, the beam processing and scanning conditions (i.e., (1) dwell time (DT) per hit point and (2) dwell point spacing (DPS)) are automatically calculated and set according to the depth of the processed region and the dose. Of course, these functions can be combined appropriately.

Accordingly, the FIB system of the structure shown in FIG. 2 yields the following advantages.

(1) The controllability can be improved by automated setting of the processing method using the scanned ion beam. In the past, the operator has been urged to select a used beam intensity according to the size of the processed region and the desired degree of finish, relying on his own knowledge and experience. However, according to the FIB system of the present embodiment, the beam diameter used for processing, dwell time per hit point, and dwell point spacing are calculated and automatically set according to the size of the processed region and the degree of finish that the operator wants.

(2) Discontinuous processing can be suppressed. In the FIB system that shoots focused ion beams, ion beams having different intensities have different beam diameters. Accordingly, in the past, the operator has had to set the dwell point spacing taking account of the ion beam diameter. According to the FIB system of the present invention, however, the dwell point spacing is automatically calculated and optimally set when the ion beam is scanned according to the used ion beam. Consequently, the dwell point spacing can be prevented from becoming too great relative to the beam diameter; otherwise, a discontinuously processed surface would be produced.

(3) Furthermore, specimen damage due to blanking tail can be suppressed. During FIB micromachining, the specimen surface is damaged by the ion beam irradiation. When the ion beam is scanned, the blanking function is necessary. That is, the beam is deflected greatly at the end of each raster line and impingement of the beam on the specimen surface is stopped. However, when blanking is carried out, the ion beam passes through specimen surface portions located outside the processed region, though in a short time. This produces damage to the specimen surface. This damage is known as blanking tail. To minimize the damage due to blanking tail, it is necessary to minimize the number of frames scanned during processing. Accordingly, in the past, the operator has had to set the dwell point spacing taking account of the number of frames. On the other hand, in the FIB system of the present embodiment, the dwell time per hit point and the dwell point spacing are automatically calculated and optimally set such that the number of frames is reduced to a bare minimum. Consequently, damage to the specimen due to blanking tail can be suppressed to a minimum.

(4) The finishing accuracy can be improved. In FIB processing utilizing scanning of a focused ion beam, if the scan speed of the beam decreases below a threshold value, the finished shape is disfigured severely. Accordingly, in the past, the operator has had to set the dwell time per hit point and the dwell point spacing taking account of the scan speed of the beam. On the other hand, according to the FIB system of the present embodiment, the dwell time per hit point and the dwell point spacing are automatically calculated and set optimally and, therefore, deterioration of the finished shape can be prevented.

Another embodiment of the present invention is next described. This embodiment provides a dual-beam (DB) system in which a FIB system and a scanning electron microscope (SEM) are combined.

Figure 8:
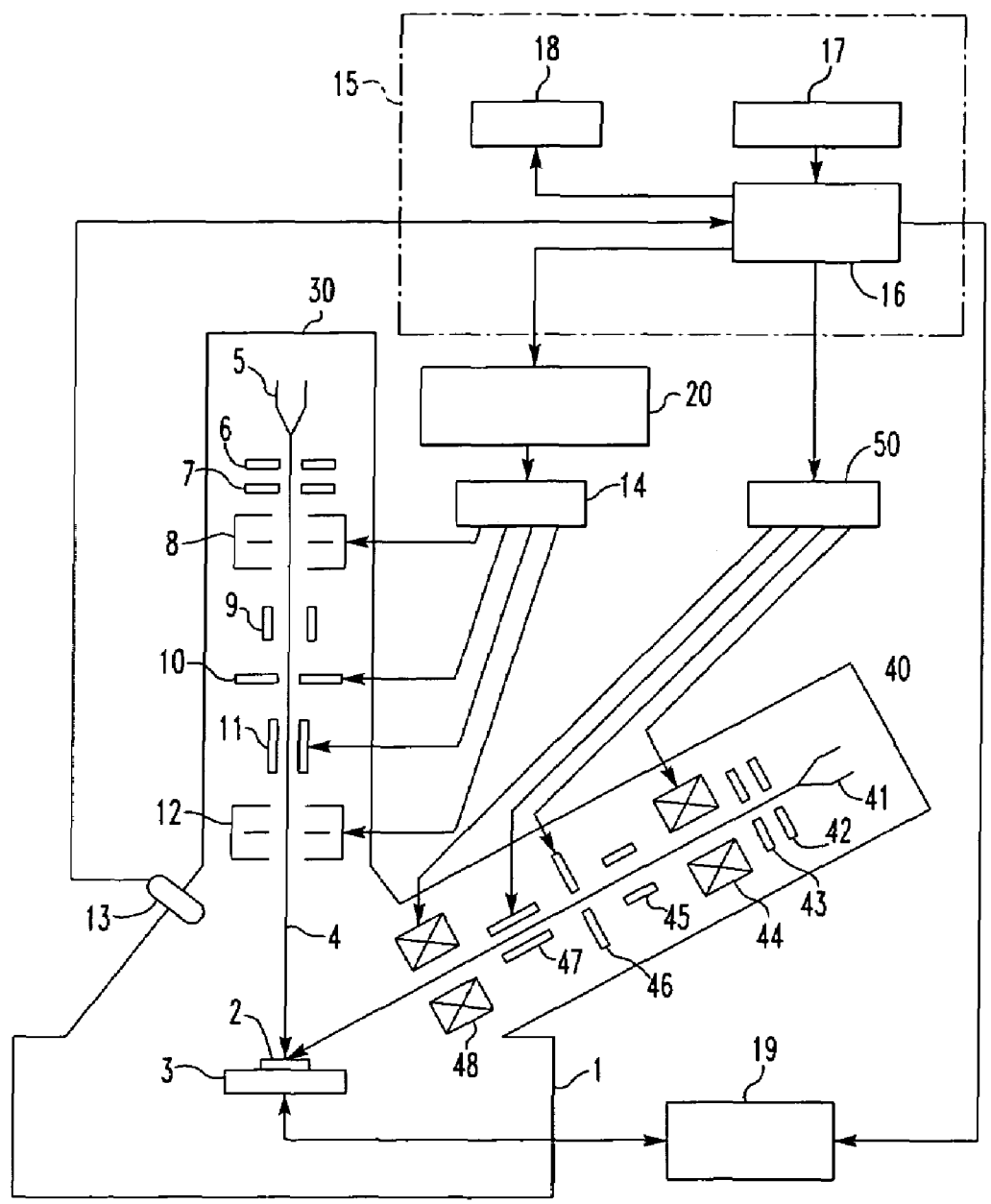
FIG. 8 is a block diagram of a dual-beam (DB) system according to another embodiment of the present invention.

FIG. 8 shows the structure of the dual-beam system. This system has an ion beam column 30 having the same structure as the FIB system already described in connection with FIG. 2. The column 30 produces an ion beam that is directed at a certain region of a specimen 2 to process the region. The processed region is scanned with an electron beam produced by an electron beam irradiation column 40 consisting of the SEM. Secondary electrons are produced in response to the electron beam scanning, and are detected by a secondary electron detector 13. Thus, a scanned image is obtained.

Included within the electron beam irradiation column 40 are an electron source 41, extraction electrodes 42 for extracting ions from the electron source 41, an anode 43, condenser lenses 44, beam-blanking electrodes 45, apertures 46, beam-deflecting electrodes 47, and an objective lens 48.

The electron source 41, condenser lenses 44, beam-blanking electrodes 45, apertures 46, beam-deflecting electrodes 47, and objective lens 48 are controlled by a SEM control portion 50. For example, where the current of the electron beam hitting the specimen 2 is varied, the amount of electron beam produced from the electron source 41 is controlled. In order to vary the beam diameter on the specimen 2, the intensities of the condenser lenses 44 and objective lens 48, for example, are controlled so as to control the degree of focusing of the electron beam. The impingement of the ion beam on the specimen 2 is turned on and off by controlling the beam-blanking electrodes 45. The electron beam scanning of the surface of the specimen 2 is controlled by the beam-deflecting electrodes 47.

The SEM control portion 50 is controlled by the computer 15 similarly to the FIB driver portion 14.

In this dual-beam (DB) system, the specimen 2 is processed by the ion beam column 30 consisting, for example, of a FIB system. This processing is performed by producing an ion beam from the ion source 5, sharply focusing the beam 4 onto the specimen 2 by the condenser lenses 8 and objective lens 12, and raster-scanning the beam over the specimen by the beam-deflecting electrodes 11. At the same time, the specimen stage 3 is moved in a direction perpendicular to the raster lines. As a result of the scanning and movement, a hole is formed in a desired region of the surface of the specimen 2 by the ion beam processing. Then, the electron beam is directed at the cross section of the hole from the electron beam irradiation column 40 consisting of the SEM to scan the cross section in two dimensions. Secondary electrons produced in response to the scanning are detected by the secondary electron detector 13. The output signal from the detector 13 is supplied to the monitor 18 via the arithmetic unit 16 and so a SEM image of the cross section of the processed portion is obtained.

Of course, the ion beam column 30 included in the dual-beam system and consisting of the FIB system operates on the principle already described in connection with FIGS. 3-5. That is, the diameter of the ion beam used for processing is automatically calculated and set according to the "size of the processed region" entered by the operator. Furthermore, the diameter of the ion beam used for processing is automatically calculated and set according to the "degree of finish". In addition, the dual-beam system automatically calculates and sets beam processing and scanning conditions (i.e., (1) dwell time (DT) per hit point and (2) dwell point spacing (DPS)) according to the diameter of the used ion beam. Additionally, the system automatically calculates and sets the beam processing and scanning conditions (i.e., (1) dwell time (DT) per hit point and (2) dwell point spacing (DPS)) according to the depth of the processed region and dose. Of course, these functions may be appropriately combined. Hence, the system yields the same advantages as the above-described system.

Having thus described my invention with the detail and particularity required by the Patent Laws, what is desired protected by Letters Patent is set forth in the following claims.

The invention claimed is:

1. A focused ion beam system for processing a specimen by irradiating the specimen with a focused ion beam, said focused ion beam system comprising:
    an ion beam source for producing the ion beam;
    condenser lenses for focusing the produced ion beam;
    multiple variable apertures for selectively limiting current of the ion beam focused by the condenser lenses;
    a deflection portion for deflecting the focused ion beam whose current has been selectively limited by the apertures;
    an objective lens for focusing the deflected ion beam at a desired position on the specimen;
    a specimen stage for moving the specimen;
    an input portion for accepting data entered by a human operator;
    a control portion comprising a computer readable medium containing instructions to cause said control portion to first select optical conditions for the condenser lenses, the multiple variable apertures, the deflection portion, and the objective lens for establishing a beam size based on the data entered into said input portion comprising the size of the processed region and the degree of precision wherein the beam size is increased for larger processing regions but not so as to provide unacceptable precision, and second automatically calculate processing and scanning conditions including dwell time per hit position, dwell position spacing and frame in accordance with said selected optical conditions and cut depth and specimen kind or dose entered into the input portion wherein the dwell position spacing is reduced sufficient to suppress discontinuous processing, the frame time is increased to reduce blanking tail to a minimum, and the hit position spacing and dwell time per hit position are set so the scan speed does not decrease below a threshold value at which the specimen is disfigured;
    a setting condition data output portion for outputting data based on the optical conditions and processing and scanning conditions selected and calculated by said control portion; and
    a driver portion for driving the condenser lenses, the multiple variable apertures, the deflection portion, and the objective lens based on the data output from said setting condition data output portion about the optical conditions and the processing and scanning conditions.

2. A focused ion beam system as set forth in claim 1, wherein said processing and scanning conditions automatically set by said control portion include a dwell time of the ion beam per hit point on the specimen and a dwell point spacing.

3. A focused ion beam system as set forth in claim 1, wherein said control portion calculates a diameter of the ion beam used for processing according to the size of the processed region on the specimen, the size being entered into said input portion, and first selects an optical condition file matched to the calculated beam diameter and based upon the degree of finish selected the optical condition file adjacent the first selected file is selected.

4. A focused ion beam system as set forth in claim 2, wherein said control portion calculates a diameter of the ion beam used for processing according to the size of the processed region on the specimen, the size being entered into said input portion, and selects an optical condition file matched to the calculated beam diameter.

5. A focused ion beam system as set forth in claim 1, wherein said control portion calculates a diameter of the ion beam used for processing according to the size of the processed region on the specimen, the size being entered into said input portion, and selects an optical condition file matched to the calculated beam diameter.

6. A focused ion beam system as set forth in claim 3, wherein said control portion automatically selects said optical condition file based on the calculated diameter of the beam, the file defining a mode of operation in which the condenser lenses, objective lens, multiple variable apertures, and deflection portion are driven by the driver portion.

7. A focused ion beam system as set forth in claim 4, wherein said control portion automatically selects said optical condition file based on the calculated diameter of the beam, the file defining a mode of operation in which the condenser lenses, objective lens, multiple variable apertures, and deflection portion are driven by the driver portion.

8. A focused ion beam system as set forth in claim 5, wherein said control portion automatically selects said optical condition file based on the calculated diameter of the beam, the file defining a mode of operation in which the condenser lenses, objective lens, multiple variable apertures, and deflection portion are driven by the driver portion.

* * * * *

UNITED STATES PATENT AND TRADEMARK OFFICE
CERTIFICATE OF CORRECTION

| | | |
|---|---|---|
| PATENT NO. | : 7,528,394 B2 | Page 1 of 1 |
| APPLICATION NO. | : 11/417504 | |
| DATED | : May 5, 2009 | |
| INVENTOR(S) | : Matsuba | |

It is certified that error appears in the above-identified patent and that said Letters Patent is hereby corrected as shown below:

<u>Column 11</u>, Line 44, Claim 1, "spacing and frame in" should read
-- spacing and frame time in --

Signed and Sealed this

First Day of September, 2009

David J. Kappos
*Director of the United States Patent and Trademark Office*